(12) United States Patent
Mentzer et al.

(10) Patent No.: US 7,710,567 B1
(45) Date of Patent: May 4, 2010

(54) SYSTEMS AND METHODS FOR DETERMINING LEVEL AND/OR TYPE OF A FLUID

(75) Inventors: Mark A. Mentzer, Lititz, PA (US); Nicholas P. Petrillo, New Cumberland, PA (US); Wayne A. Webb, Lancaster, PA (US); Brian S. Trostle, York Springs, PA (US)

(73) Assignee: Strube, Inc., Marietta, PA (US)

( * ) Notice: Subject to any disclaimer, the term of this patent is extended or adjusted under 35 U.S.C. 154(b) by 367 days.

(21) Appl. No.: 11/668,624

(22) Filed: Jan. 30, 2007

Related U.S. Application Data

(60) Provisional application No. 60/830,903, filed on Jul. 14, 2006, provisional application No. 60/782,583, filed on Mar. 14, 2006.

(51) Int. Cl.
*G01N 21/00* (2006.01)
*G01N 21/59* (2006.01)

(52) U.S. Cl. .................. 356/436; 356/432; 250/577; 73/293

(58) Field of Classification Search ......... 356/432–436, 356/4.01, 3.01, 5.01, 5.1; 250/577, 573, 250/903, 904, 227.14, 227.25; 73/293, 311, 73/313, 314, 319
See application file for complete search history.

(56) References Cited

U.S. PATENT DOCUMENTS

| | | | | |
|---|---|---|---|---|
| 3,120,125 | A * | 2/1964 | Vasel | 73/293 |
| 4,119,860 | A * | 10/1978 | Gooley | 250/577 |
| 4,284,884 | A   | 8/1981 | Dyment et al. | 250/205 |
| 4,355,238 | A * | 10/1982 | Ruell | 250/577 |
| 4,450,722 | A * | 5/1984 | Keyes et al. | 73/293 |
| 4,521,683 | A * | 6/1985 | Miller | 250/221 |
| 4,564,292 | A * | 1/1986 | Omet | 356/133 |
| 4,745,293 | A * | 5/1988 | Christensen | 250/577 |
| 4,821,570 | A * | 4/1989 | Khoi | 73/309 |

(Continued)

OTHER PUBLICATIONS

U.S. Appl. No. 11/649,109, filed Jan. 3, 2007, Mentzer, et al.
U.S. Appl. No. 11/649,142, filed Jan. 3, 2007, Mentzer, et al.
"Agilent Technologies Application Brief, 1-007," *Projection of Long Term Light Output Performance for AS AlInGaP LED Technology*, 1999, 2 pages.

(Continued)

*Primary Examiner*—Sang Nguyen
(74) *Attorney, Agent, or Firm*—Smith, Gambrell & Russell, LLP

(57) ABSTRACT

Methods and systems are provided for determining the density and/or temperature of a fluid based on the manner in which optical energy is affected as the optical energy propagates across a gap between opposing end faces of optical waveguides, or the manner in which the optical energy is reflected from interfaces of optical waveguides and the fluid.

16 Claims, 13 Drawing Sheets

U.S. PATENT DOCUMENTS

| | | | | |
|---|---|---|---|---|
| 4,950,885 | A | * | 8/1990 | Kershaw ................ 250/227.25 |
| 4,994,682 | A | * | 2/1991 | Woodside .................. 250/577 |
| 5,073,720 | A | * | 12/1991 | Brown ........................ 250/577 |
| 5,331,850 | A | * | 7/1994 | Loos ............................ 73/293 |
| 5,425,624 | A | * | 6/1995 | Williams ..................... 417/36 |
| 5,743,135 | A | * | 4/1998 | Sayka et al. .................. 73/293 |
| 6,040,897 | A | * | 3/2000 | Clifford et al. ............. 356/4.01 |
| 6,541,758 | B2 | * | 4/2003 | Yashiro et al. ......... 250/227.14 |
| 6,831,290 | B2 | | 12/2004 | Mentzer |
| 7,259,384 | B2 | * | 8/2007 | Hariram et al. ............. 250/577 |

OTHER PUBLICATIONS

*Handbook of Aviation Fuel Properties*, 3$^{rd}$ Ed., CRC Report No. 635, 2004, iii-xiv, 1-1-4-18.

Meyrath, T.P., *Multipurpose Analog PID Controller*, Todd P. Meyrath, Atom Optics Laboratory Center for Nonlinear Dynamics, University of Texas at Austin, Mar. 14, 2000, 1-6.

Simpson, J.O., et al., "Fundamental insight on developing low dielectric constant polyimides," NASA Langley Res. Center, 1-19.

\* cited by examiner

SYSTEMS AND METHODS FOR DETERMINING LEVEL AND/OR TYPE OF A FLUID

This application claims priority under 35 U.S.C. §119(e) to U.S. provisional application No. 60/830,903, filed Jul. 14, 2006; and U.S. provisional application No. 60/782,583, filed Mar. 14, 2006. The contents of each of these applications is incorporated by reference herein in its entirety.

TECHNICAL FIELD

The present application relates to systems and methods for measuring the level of a fluid in a container, and/or identifying the type of fluid or fluids in the container.

BACKGROUND

A need to continuously measure the level of a fluid exists in many commercial and military applications. For example, fluid-level sensors are commonly used in the fuel tanks of aircraft, automobiles, and trucks. Fluid-level sensors are also used to monitor fluid levels within tanks utilized for fuel dispensing, wastewater treatment, chemical storage, food processing, etc.

Electrical fluid-level sensors present safety-related issues in many applications. For example, electrical fluid-level sensors have the potential to generate sparks, and thus present an explosion hazard when used in the presence of flammable fluids. In particular, the electrical current associated with an electrical fluid-level sensor has the potential to introduce a spark due to, for example, chaffed insulation on the wiring that carries electrical current to or from the sensor. A spark can ignite explosive vapors that may be present in the tank in which the sensor is located.

Moreover, electrical sensors are susceptible to signal degradation in the presence of electromagnetic interference.

Electrical fluid-level sensors can include a float mechanically or magnetically coupled to an external gauge. Alternatively, electrical fluid-level sensors can operate on the principle that the dielectric constant between electrical conductors immersed or partially immersed in a fluid changes with the fluid level. This type of sensor, however, when used to detect fuel levels, can lose accuracy as the amount of water and other contaminates in the fuel increases.

The presence of contaminates in the fluid can result in additional problems. For example, water is often present in aircraft fuel tanks due to factors such as the introduction of contaminated fuel into the tank, condensation within the tank, and infiltration during fueling in adverse weather conditions. Water-contaminated fuel can result in degraded engine performance, and in extreme cases, can cause a complete engine stoppage.

An ongoing need therefore exists for a system that can determine the level and/or type of a fluid in a tank or other container without introducing electrical current into the tank or container, and that can function in a satisfactory manner in the presence of contaminates and/or electromagnetic interference.

SUMMARY OF THE INVENTION

Methods and systems are provided for determining the density and/or temperature of a fluid based on the manner in which optical energy is affected as the optical energy propagates across a gap between opposing end faces of optical waveguides, or the manner in which the optical energy is reflected from interfaces of optical waveguides and the fluid.

Methods comprise directing optical energy through a first plurality of optical waveguides each having an end face immersed in one or more types of fluids, and measuring the optical energy that is transmitted through the one or more types of fluids to a second plurality of optical waveguides each having an end face that opposes and is spaced apart from an associated one of the end faces of the first plurality of optical waveguides. Methods also comprise determining a level or levels of the one or more fluids based on (i) the optical energy that is transmitted through the one or more types of fluids, and (ii) relative locations of the end faces of the first and/or second plurality of optical waveguides.

Embodiments of systems comprise a first plurality of optical waveguides each having an end face capable of being immersed in one or more types of fluids in a container, and a second plurality of optical waveguides each having an end face that opposes an associated end face of one of first plurality of optical waveguides and is spaced apart from the associated end face of the one of first plurality of optical waveguides by a gap.

The embodiments also comprise one or more sources of optical energy in optical communication with the first plurality of optical waveguides, one or more detectors of optical energy in optical communication with the second plurality of optical waveguides, and a computing device communicatively coupled to the one or more detectors of optical energy. The computing device is capable of determining a level of the fluid in the container based on an intensity of the optical energy incident upon the one or more detectors of optical energy and relative locations of the end faces of the first and/or second plurality of optical waveguides.

Other methods comprise transmitting optical energy through a first plurality of optical waveguides having ends arranged at different heights in a container holding a fluid, and identifying which of the ends of the first plurality of optical waveguides are immersed in the fluid based on attenuation of the optical energy after the optical energy exits the first plurality of optical waveguides. The methods also comprise determining a level of the fluid within the container based on the locations of the ends of the first plurality of optical waveguides.

Other methods comprise directing optical energy at a gap defined by opposing end faces of a first and a second optical waveguide, and determining a type of fluid present in the gap based on a predetermined relationship between the identity of the fluid and an intensity of the optical energy after the optical energy crosses the gap and enters the second optical waveguide.

Other methods comprise illuminating end faces of optical waveguides immersed in one or more types of fluids with optical energy, and measuring the optical energy that is transmitted through or reflected from interfaces of the one or more optical waveguides and the one or more types of fluids. The methods also comprise determining a level or levels of the one or more fluids based on (i) the optical energy that passes through or is reflected from the interfaces of the one or more optical waveguides and the one or more fluids, and (ii) relative locations of the end faces.

Other embodiments of systems comprise a plurality of optical waveguides each having an end face capable of being immersed in one or more types of fluids in a container, and one or more sources of optical energy in optical communication with the plurality of optical waveguides. The systems also comprise one or more detectors of optical energy in optical communication with the plurality of optical waveguides, and a computing device communicatively coupled to the one or more detectors of optical energy. The computing device is capable of determining a level of the fluid in the container based on an intensity of the optical energy incident upon the one or more detectors of optical energy and relative locations of the end faces of the optical waveguides.

BRIEF DESCRIPTION OF THE DRAWINGS

The foregoing summary, as well as the following detailed description of embodiments, are better understood when read in conjunction with the appended diagrammatic drawings. For the purpose of illustrating the embodiments, the drawings diagrammatically depict specific embodiments. The appended claims are not limited, however, to the specific embodiments disclosed in the drawings. In the drawings:

DETAILED DESCRIPTION OF ILLUSTRATIVE EMBODIMENTS

Figure 1:
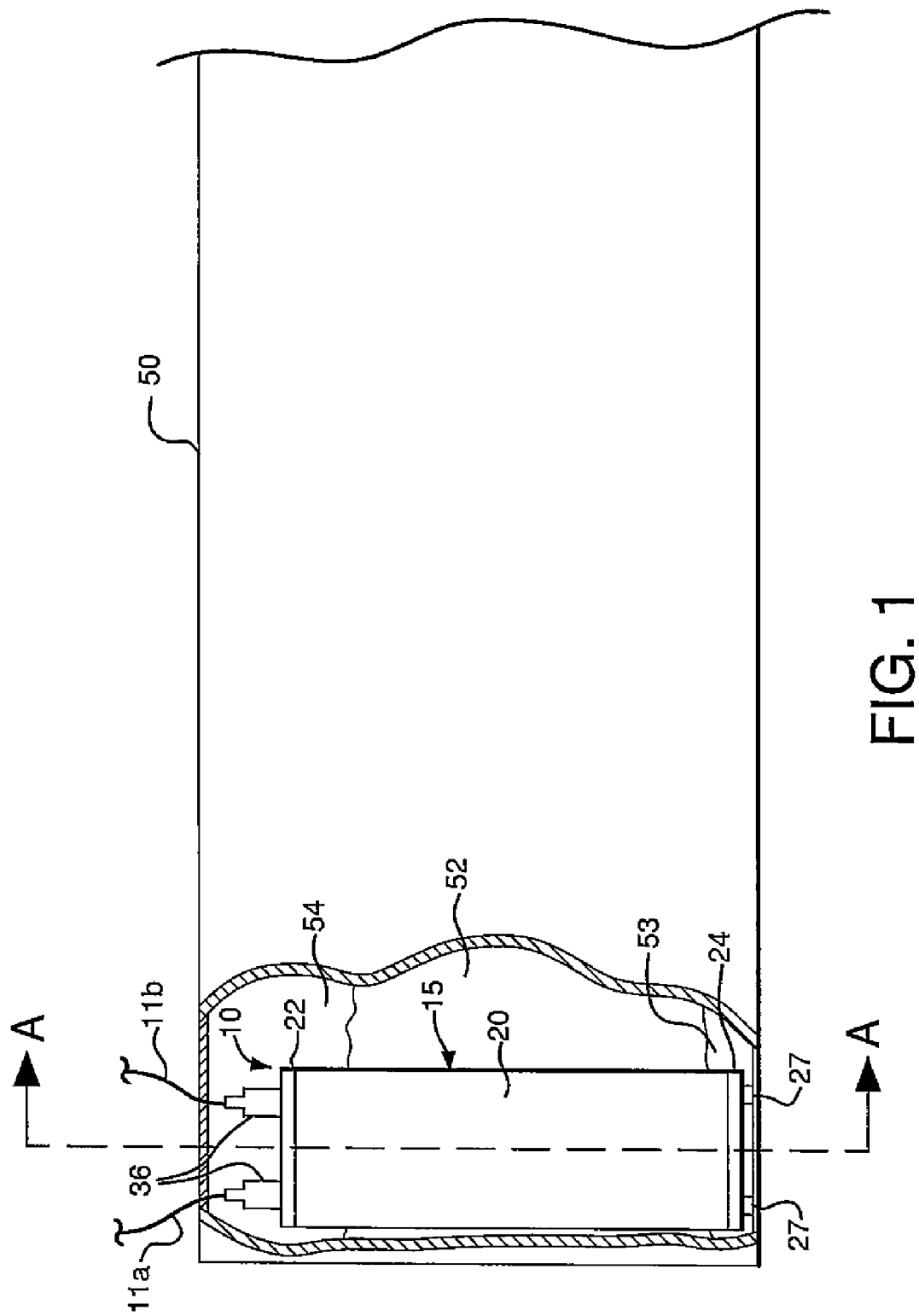
FIG. 1 depicts an embodiment of a system for measuring the level and/or type of a fluid in a container, showing a housing of the system installed in a container, and depicting the container in a partial cutaway view.

FIGS. 1-8 depict an embodiment of a system 10 for measuring the level of a fluid in a container such as a tank 50. The system 10 comprises a housing 15. The housing 15 is positioned within the tank 50 as depicted in FIG. 1, so that the fluid fully or partially immerses the housing 15.

Figure 2:
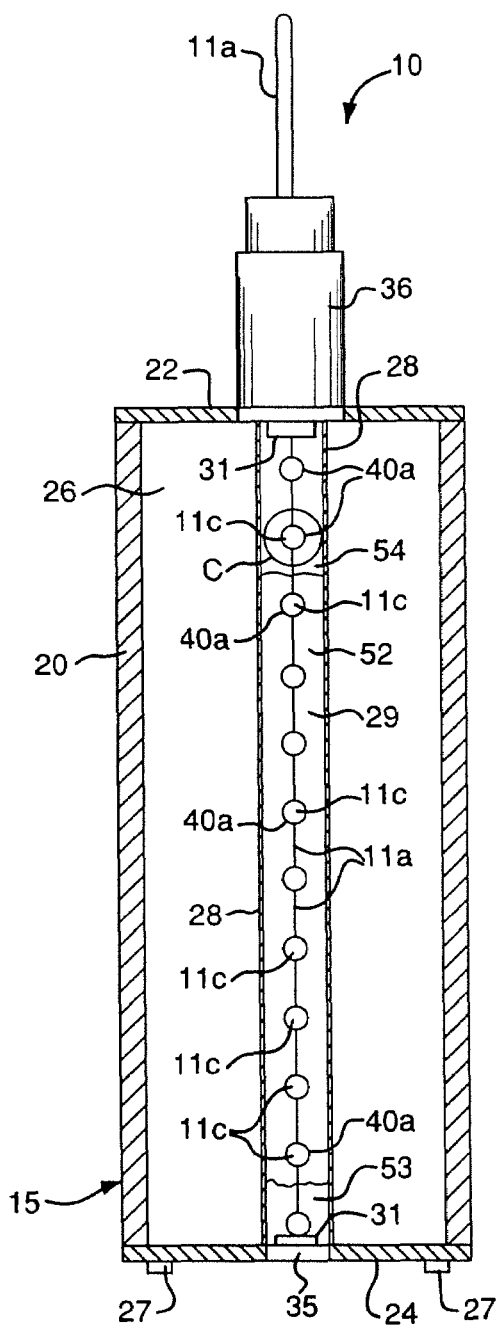
FIG. 2 is a cross-sectional view of the housing shown in FIG. 1, taken through the line "A-A" of FIG. 1.
Figure 3:
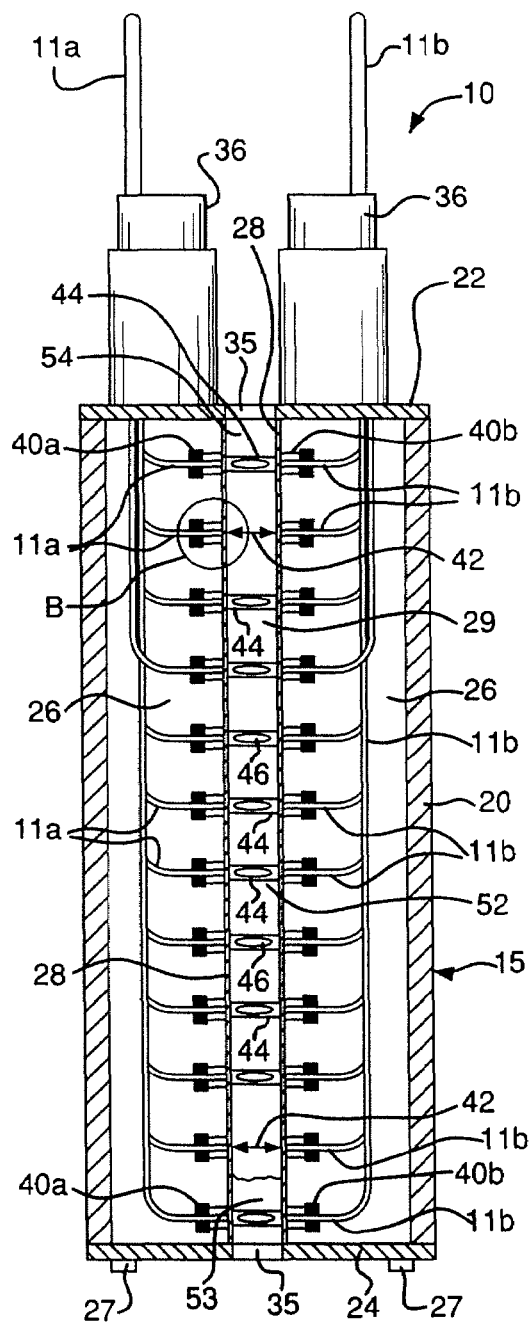
FIG. 3 is a cross-sectional view of the housing shown in FIGS. 1 and 2, from a perspective rotated approximately ninety degrees from the perspective of FIG. 2.

The housing 15 includes a cylindrical body 20, a top portion 22, and a bottom portion 24. The body 20 can have other shapes in alternative embodiments. The top and bottom portions 22, 24 can be secured to the body 20 by a suitable means such as fasteners. The body 20, top portion 22, and bottom portion 24 define a volume 26 within the housing 15, as shown in FIGS. 2 and 3. The housing 15 can also include gaskets (not shown) positioned between the body 20 and each of the top and bottom portions 22, 24, to help seal the volume 26. Legs 27 can be attached to the bottom portion 24 to space the bottom portion 24 from the bottom surface of the tank 50, as shown in FIG. 1.

The housing 15 also includes a cylindrical conduit 28, as shown in FIGS. 2 and 3. The conduit 28 is positioned in the volume 26 within the housing 15. The conduit 28 extends along the centerline of the housing 15, between the top and bottom portions 22, 24. A lip 31 can be formed on an inwardly-facing surface of each of the top and bottom potions 22, 24. The lips 31 engage an inner circumference of the conduit 28. An O-ring seal (not shown) can be positioned between the interface of the conduit 28 and each of the lips 31.

The body 20 and the conduit 28 are each depicted as cylindrical for exemplary purposes only. The body 20 and the conduit 28 can have other shapes in alternative embodiments. The housing 15 should be formed from a material or materials that are compatible the fluids within the tank in which the housing 15 is to be located.

Figure 4:
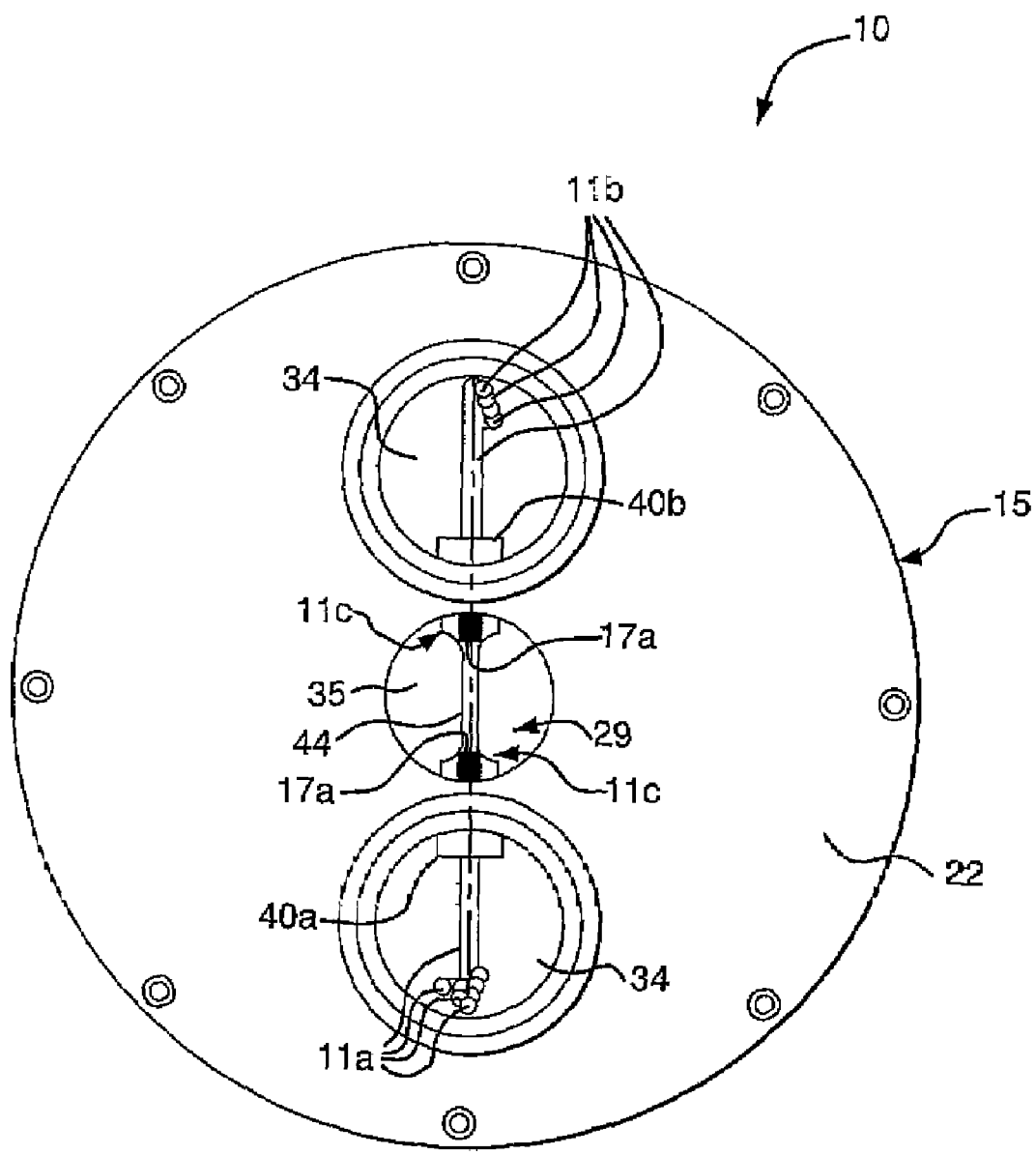
FIG. 4 is a top view of the housing shown in FIGS. 1-3, with sleeves that convey fiber optic cables into the housing not shown for clarity of illustration.

The interior volume of the conduit 28 defines a passage 29 through the housing 15, as shown in FIGS. 2 through 4. The top and bottom portions 22, 24 each have a through hole 35 formed therein. The through holes 35 are aligned with the passage 29 defined by the conduit 28. The through holes 35 permit the fluid in the tank 50 to enter the passage 29 when the housing 15 is immersed in the fluid. The through holes 35 also permit the level of the fluid in the passage 29 to rise and fall with the level of the fluid in the tank 50, so that the fluid level in the passage 29 is about the same as the fluid level in the tank 50.

Figure 5:
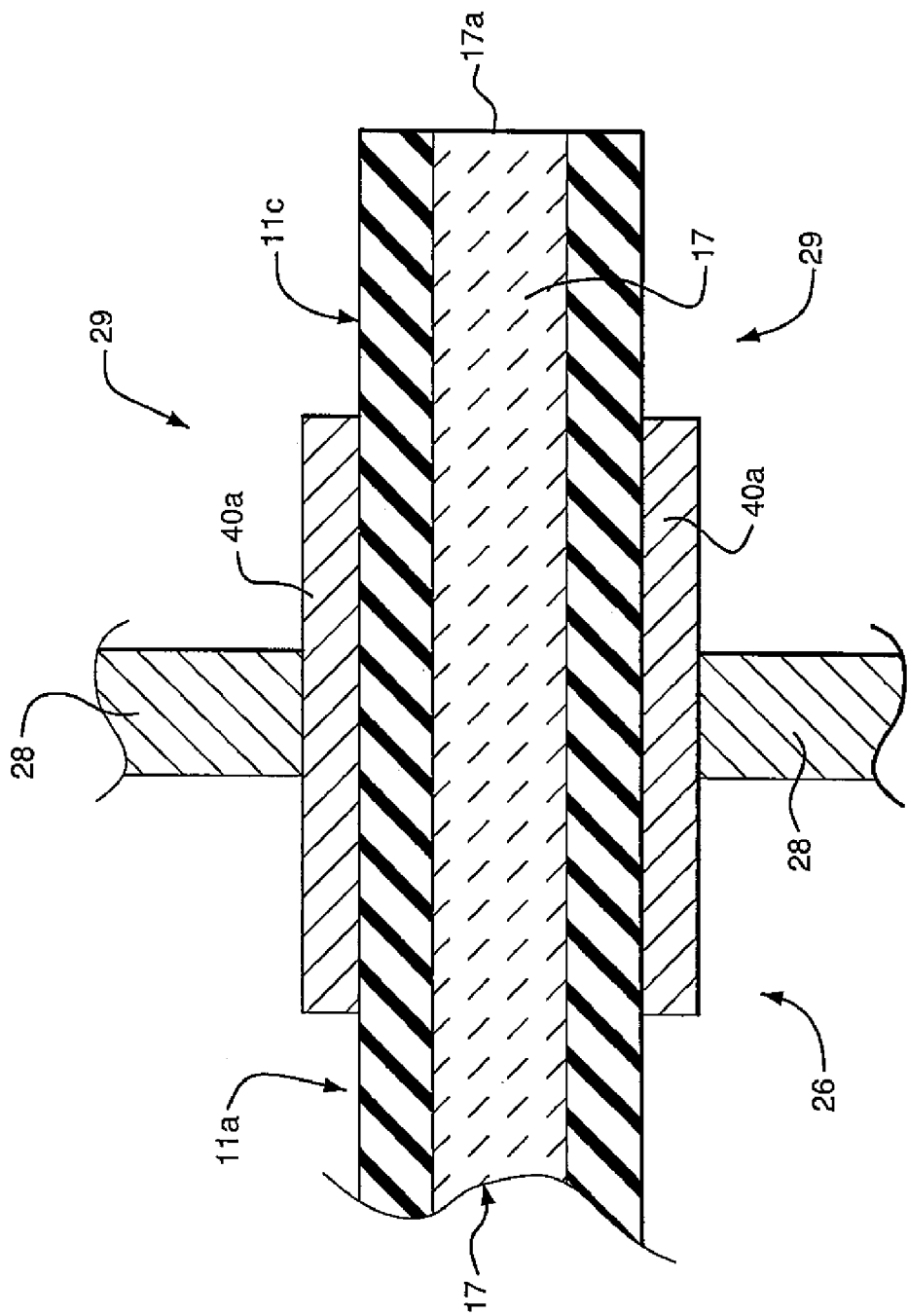
FIG. 5 is a magnified view of the area designated "B" in FIG. 3.
Figure 6:
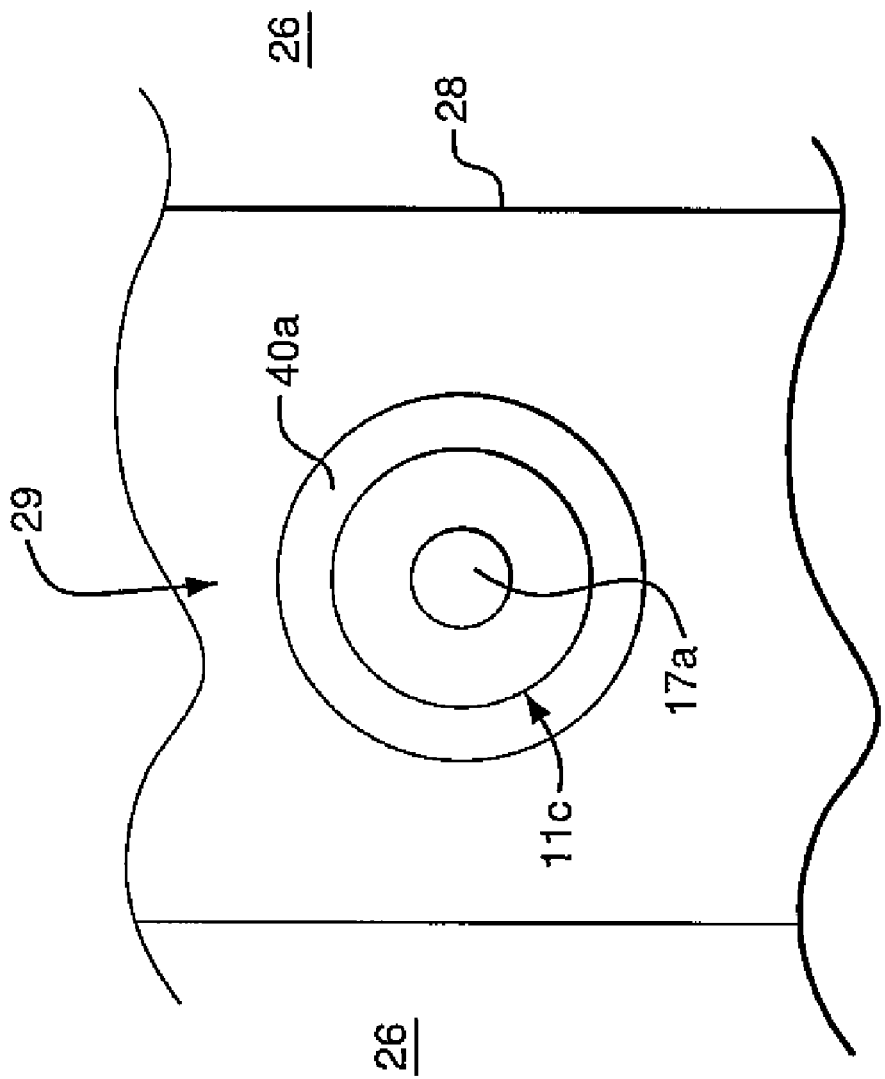
FIG. 6 is a magnified view of the area designated "C" in FIG. 2.

The system 10 also comprises a first plurality of fiber optic cables 11a, and a second plurality of fiber optic cables 11b. Each fiber optic cable 11a, 11b comprises a single optical fiber 17 that functions as a waveguide. The optical fibers 17 are shown in FIGS. 5 and 6. Alternative embodiments can include fiber optic cables having more than one optical fiber.

The fiber optic cables 11a, 11b extend though the top portion 22 of the housing 15 and into the interior volume 26 by way of through holes 34 formed in the top portion 22 and depicted in FIG. 4. In particular, the fiber optic cables 11a extend through a sleeve 36, and the fiber optic cables 11b extend through another sleeve 36. The sleeves 36 mate with the top portion 22 so that each sleeve 36 is partially disposed in a respective through hole 34. The sleeves 36 and the top portion 22 can mate by a suitable means such as complementary threads.

The system 10 also includes a first plurality of sleeves 40a and a second plurality of sleeves 40b, as shown in FIGS. 2 through 6. The sleeves 40a, 40b are mounted on the conduit 28 by a suitable means such as a press fit. The sleeves 40a are arranged in a first vertical column located on one side of the conduit 28, as shown in FIGS. 2 and 3. The sleeves 40b are arranged in a second vertical column located on the other side of the conduit 28, as shown in FIGS. 3 and 4, so that each sleeve 40a diametrically opposes an associated one of the sleeves 40b.

Each fiber optic cable 11a extends through an associated sleeve 40a so that an end portion 11c of the fiber optic cable 11a is positioned in the passage 29, as shown in FIGS. 2, 4, and 5. Each fiber optic cable 11b likewise extends through an associated sleeve 40b so that an end portion 11c of the fiber optic cable 11b is positioned in the passage 29. Each end portion 11c of the fiber optic cables 11a opposes the end portion 11c of an associated one of the fiber optic cables 11b, due to the diametrically opposed relationship of the sleeves 40a, 40b. The end portions 11c of the fiber optic cables 11a and the end portions 11c of the fiber optic cables 11b form two vertical stacks within the passage 29 due to the stacked arrangement of the sleeves 40a, 40b.

The sleeves 40a, 40b and the end portions 11c of the fiber optic cables 11a, 11b can be stacked in arrangements other than vertical in alternative embodiments. For example, the sleeves 40a, 40b and the end portions 11c can be stacked in a helical or diagonally-opposed relationship in alternative embodiments.

Each optical fiber 17 has an end face 17a that forms part of the end portion 11c of the associated fiber optic cable 11a, 11b. The end face 17a of the optical fiber 17 of each fiber optic cable 11a is spaced apart from an end face 17a of the optical fiber 17 of the associated fiber optic cable 11b by a gap 42, shown in FIGS. 3 and 7.

Each pair of associated end portions 11c of the fiber optic cables 11a, 11b is positioned in an alignment guide 44, as shown in FIGS. 2 and 4 (two of the alignment guides are not shown in FIG. 3, for clarity of illustration). The ends of each alignment guide 44 are connected to an associated pair of sleeves 40a, 40b by a suitable means such as complementary threads. The alignment guides 44 maintain the axes of the optical fibers 17 within the opposing end portions 11c in a state of alignment across the associated gap 42.

The end of each optical fiber 17 of the fiber optic cables 11a, 11b is cleaved, and the exposed end face 17a of the optical fiber 17 is polished using a suitable technique such as lapping. The alignment guides 44 have openings formed therein, such as slots 46 shown in FIG. 3. The slots 46 permit fluid to enter the interior of the alignment guides 44 and immerse end faces 17a of the associated optical fibers 17.

The system 10 is depicted with twelve of the fiber optic cables 11a and twelve of the fiber optic cables 11b for exemplary purposes only. The optimal number of fiber optic cables 11a, 11b is application-dependent, and can vary with factors such as the depth of the tank or other container with which the system 10 is to be used, and the desired resolution to which the fluid level in the tank is to be measured.

Figure 7:
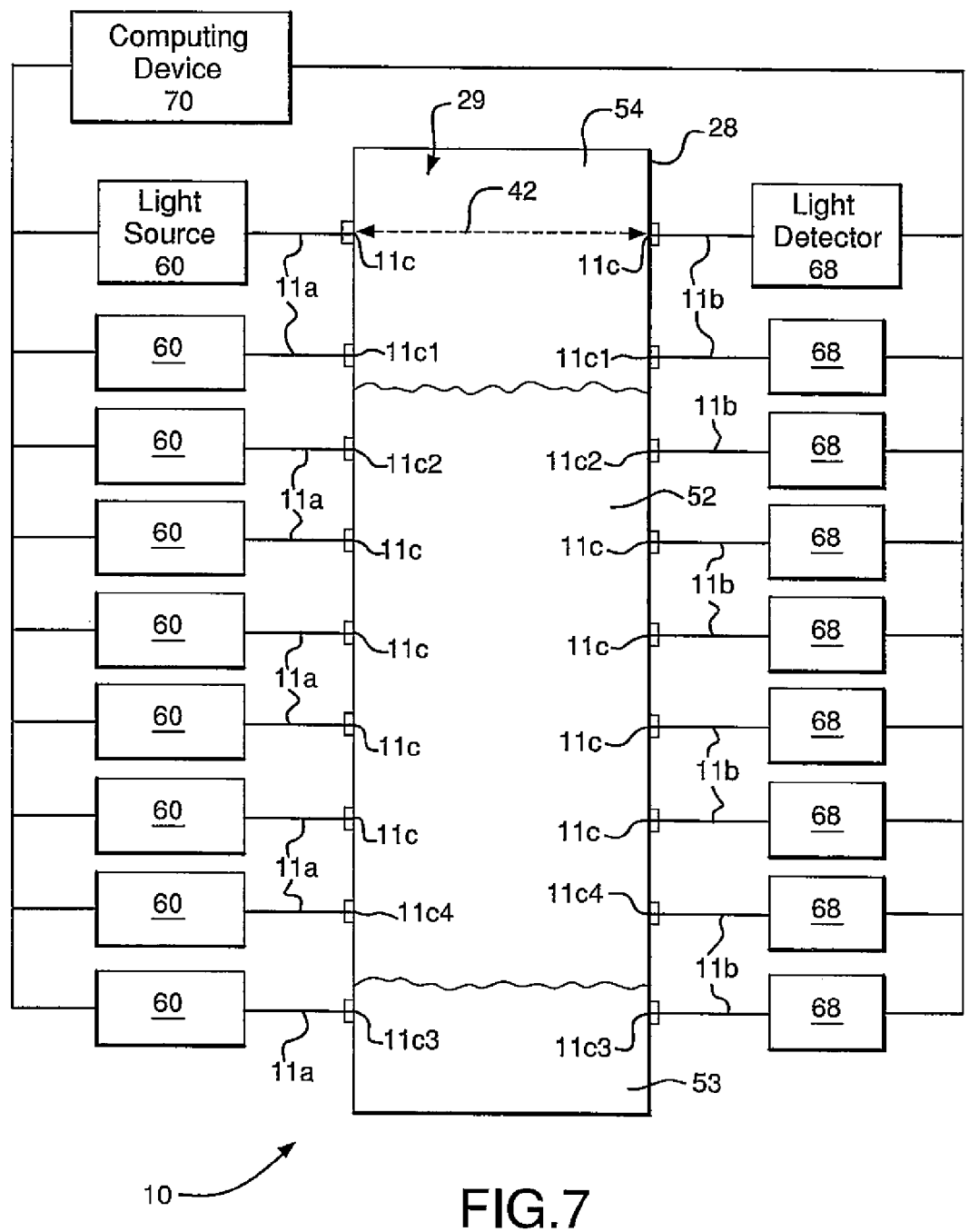
FIG. 7 is a block diagram of the system shown in FIGS. 1-5.

The system 10 further comprises a plurality of sources of optical energy such as light sources 60, depicted in FIG. 7. Each light source 60 is in optical communication with an associated one of the fiber optic cables 11a. The light sources 60 can be, for example, a light-emitting diode such as a Nichia Corp. NFSG036BT LED having emission in the visible green wavelength.

The system 10 also comprises a plurality of detectors of optical energy such as light detectors 68, also depicted in FIG. 7. Each light detector 68 is in optical communication with an associated one of the fiber optic cables 11b. The light detectors 68 can be photodetectors. For example, photodetectors such as Hamatsu S8745-01 photodetectors can be used when the light sources 60 emit in the visible green wavelength. Other types of detectors of optical energy, such as optical power meters, can be used in the alternative.

The system 10 further comprises a computing device 70 communicatively coupled to the light detectors 68. The computing device 70 can be communicatively coupled to the light sources 60, so that the computing device 70 can activate and deactivate the light sources 62. Alternative embodiments can be configured so that the light source 62 are not communicatively coupled to the computing device 70, and are not activated or deactivated by the computing device 70.

Figure 8:
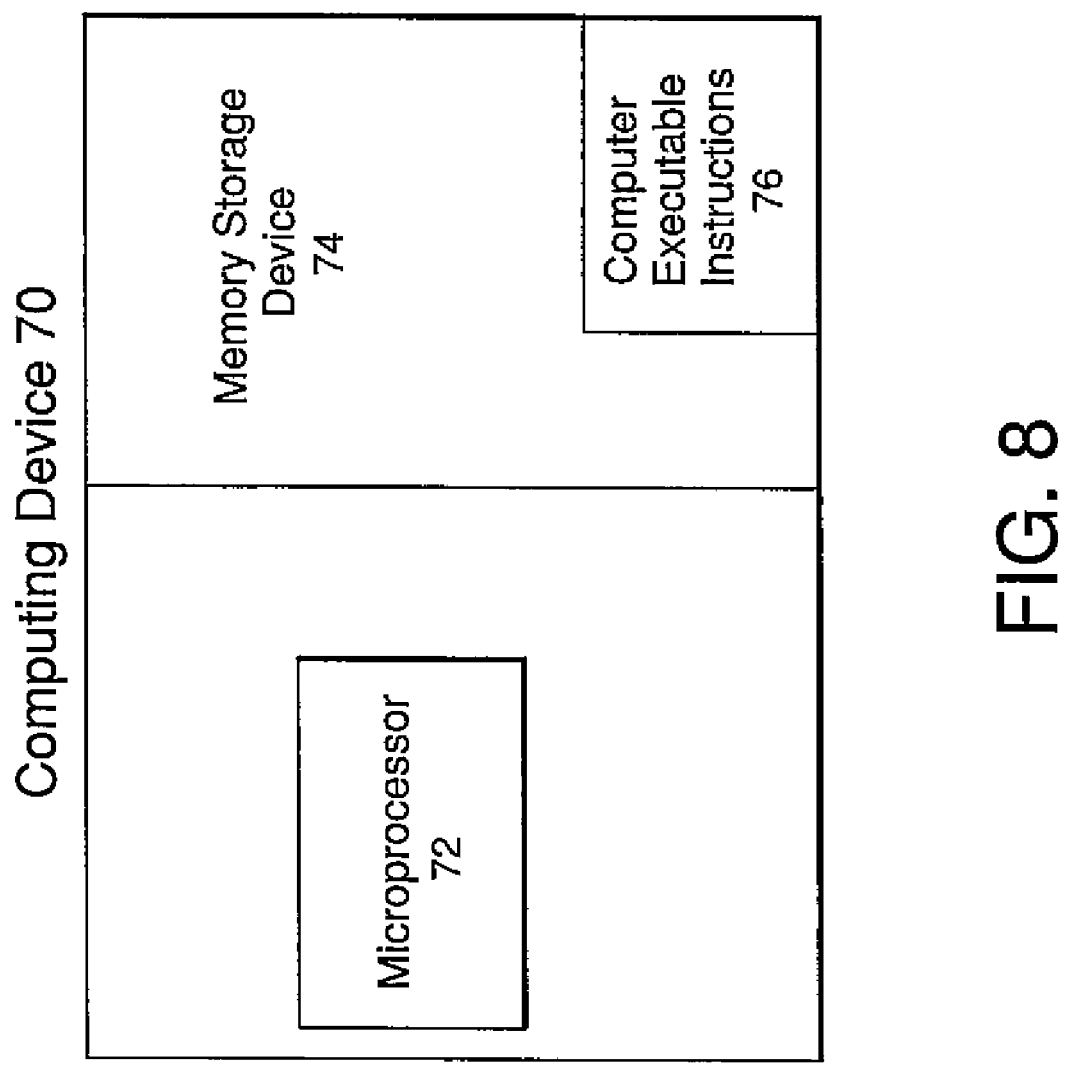
FIG. 8 is a block diagram of a computing device of the system shown in FIGS. 1-6.

The computing device 70 can include a processor such as a microprocessor 72 depicted in FIG. 8. The computing device 70 can also include a memory-storage device 74 communicatively coupled to the microprocessor 72. The computing device 70 can further include a set of computer-executable instructions 75 stored on the memory-storage device 74.

The computing device 70 can be programmed to generate an indication of the fluid level in the tank 50, as follows.

Optical energy generated by each light source 60 is transmitted through the optical fiber 17 of the associated fiber optic cable 11a. The end portions 11c of each associated pair of fiber optic cables 11a, 11b are positioned so that the axes of the associated optical fibers 17 are substantially aligned, as discussed above. A portion of the optical energy that reaches the end face 17a of each optical fiber 17 of the fiber optic cables 11a traverses the gap 42, and is incident upon the end face 17a of the optical fiber 17 of the associated fiber optic cable 11b. A portion of the optical energy incident upon the end face 17a is transmitted to one of the light detectors 68 by the optical fiber 17 of the fiber optic cable 11b. The light detector 68 generates an electrical output proportional to the intensity of the optical energy that reaches the light detector 68.

As discussed above, detectors of optical energy other than light detectors can be used in alternative embodiments. In applications where an optical power meter is used as the detector of optical energy, the intensity of the reflected light can be measured directly, i.e., without being converted to an electrical current as in the light detector 68.

The response of the light detector 68 is proportional to the amount of optical energy that traverses, or propagates across the gap 42 and enters the optical fiber 17 of the associated fiber optic cable 11b. The amount of optical energy that propagates across the gap 42 and enters the optical fiber 17, in turn, is dependent upon the type of fluid present in the gap 42. It is believed that the fluid present in the gap 42 absorbs and scatters a portion of the optical energy that exits the fiber optic cable 11a, and thereby reduces the amount of optical energy that reaches the light detector 68. The amount of optical energy that is absorbed by the fluid is dependent upon the type of fluid. The amount of optical energy that propagates across the gap 42 and is registered by the light detector 68 can therefore be correlated with the type of fluid present in the gap 42.

The tank 50 can be vented so that ambient air can enter the tank 50 as the fluid level therein decreases. Other fluids such as nitrogen gas can be used to vent the tank in the alternative. The housing 15 is configured so that the level of the fluid in the passage 29 within the conduit 28 remains about the same as the level of the fluid in the tank 50, as discussed above.

The tank 50 is depicted in FIG. 1 with a layer of a fluid, a layer of air, and a layer of water, designated respectively by the reference characters 52, 53, and 54. The fluid 52, water 53, or air 54 may be present in each gap 42 between the associated pairs of fiber optic cables 11a, 11b, depending on the respective levels of the fluid 52 and water 53 in the tank 50.

The respective levels of the fluid 52 and water 53 within the conduit 28 rise and fall in a corresponding manner with levels of the fluid 52 and water 53 in the tank 50, as noted above. The fluid 52, air 54, or water 53 therefore is present in each gap 42 within the conduit 28, depending on the level of the fluid 52 and water 53 in the tank 50. The specific gaps 42 in which fluid 52, air 54, or water 53 are present depends upon the respective levels of the fluid 52 and water 53 in the tank 50.

The output of each light detector 68 is dependent upon the type of fluid present in the associated gap 42, as discussed previously. Calibrations can be performed to correlate the output of the light detectors 68 with the presence of specific types of fluids in the gaps 42. The calibration results can be input to the computing device 70, so that the computing device 70 can recognize a particular output, or range of outputs for the light detectors 68 as an indication that a particular type of fluid (including air) is present in the gap 42 associated with a particular light detector 68. The calibration for each fluid can be conducted over a range of temperatures, to account for temperature-related changes in the indexes of refraction of the fluids.

In applications where the outputs of the light detectors 68 vary by relatively small amounts in the presence of the different types of fluids in the gaps 42, the output of the LED can be stabilized as discussed in U.S. application Ser. No. 11/649, 142 titled "Systems and Methods for Generating Optical Energy Using a Light-Emitting Diode," filed on Jan. 3, 2007, the contents of which is incorporated by reference herein in its entirety.

The end portions 11c of the fiber optic cables 11b are stacked vertically within the conduit 28, as noted above. The computing device 70 can programmed with the relative vertical position of each end portion 11c, and with the identity of the corresponding light detector 68. The location of each end portion 11c can thereby be referenced to a particular vertical position, or height within the tank 50.

The computing device 70 can be programmed to identify the respective levels of the fluid 52 and water 53 in the conduit 28 based on the relative locations of the end portions 11c of the fiber optic cables 11b, and the output levels of the light detectors 68. More particularly, the computing device 70 can be programmed to identify the uppermost end portion 11c whose associated light detector 68 has an output indicative of the presence of the fluid 52. Because the level of the fluid 52 in the conduit 28 corresponds to the level of the fluid 52 in the tank 50, the location of the uppermost end portion 11c associated with the presence of the fluid 52 is representative of the level of the fluid 52 in the tank 50.

The level of the water 53 in the tank 50 can be determined in a similar manner. More particularly, the computing device 70 can be programmed to identify the uppermost end portion 11c whose associated light detector 68 has an output indicative of the presence of the water 53. Because the level of the water 53 in the conduit 28 corresponds to the level of the water 53 in the tank 50, the location of the uppermost end portion 11c associated with the presence of the water 53 is representative of the level of the water 53 in the tank 50.

For example, FIGS. 2, 3, and 7 depict the level of the fluid 52 as being slightly below the end portions 11c occupying the second highest positions in their respective stacks. These particular end portions 11c are denoted by the reference characters 11c1 in FIG. 7, and are associated with a light detector 68 having an output indicative of the presence of air 54 in this particular example. The end portions 11c occupying the third highest positions in their respective stacks are the uppermost end portions 11c associated with a light detector 68 having an output indicative of the presence of fluid 52. These particular end portions 11c are denoted by the reference characters 11c2 in FIG. 7. The computing device 70 therefore determines the level of the fluid 52 in the tank 50 as corresponding to the vertical location of the end portions 11c2 in this particular example.

FIGS. 2, 3, and 7 depict the level of the water 53 as being slightly above the end portions 11c occupying the lowermost positions in their respective stacks. These particular end portions 11c are denoted by the reference characters 11c3 in FIG. 7, and are associated with a light detector 68 having an output indicative of the presence of water 53 in this particular example. The end portions 11c occupying the second lowermost positions in their respective stacks will be associated with a light detector 68 having an output indicative of the presence of fluid 52. These particular end portions 11c are denoted by the reference characters 11c4 in FIG. 7. The end portions 11c3 therefore are the uppermost end portions 11c associated with a light detector 68 having an output indicative of the presence of water 53, and the computing device 70 identifies the level of the water 53 in the tank 50 as corresponding to the vertical location of the end portions 11c3 in this particular example.

The computing device 70 can also be programmed to recognize the level of a fluid in the tank 50 without identifying the fluid type. In particular, the computing device 70 can be programmed to compare the outputs of the light detectors 68 associated with end portions 11c that occupy adjacent positions in the stack, and to recognize a difference between the outputs above a predetermined threshold as an indication that the associated end portions 11c are immersed in different types of fluids.

For example, the outputs of the light detectors 68 associated with the end portions 11c1 and 11c2 will be substantially different because the end portions 11c1 and 11c2 are immersed in fluids that attenuate the optical energy incident thereupon to different extents. The computing device 70 can be programmed to recognize this difference as an indication that the level of a fluid in the tank 50 corresponds to the vertical position of the end portions 11c1, the vertical position of the end portions 11c2, or a vertical position between those of the end portions 11c1, 11c2.

The system 10 can further include a display (not shown) communicatively coupled to the computing device 70. The fluid-level and fluid-type information generated by the computing device 70 can be transmitted to the display. The fluid-level and fluid-type information can be transmitted to other devices, such as a remote computer, for further processing, display, or storage.

FIGS. 9-17 depict alternative embodiments of the system 10. Some of these embodiments are configured so that fewer light sources 60 and/or light detectors 68 are used in comparison to the system 10.

Figure 9:
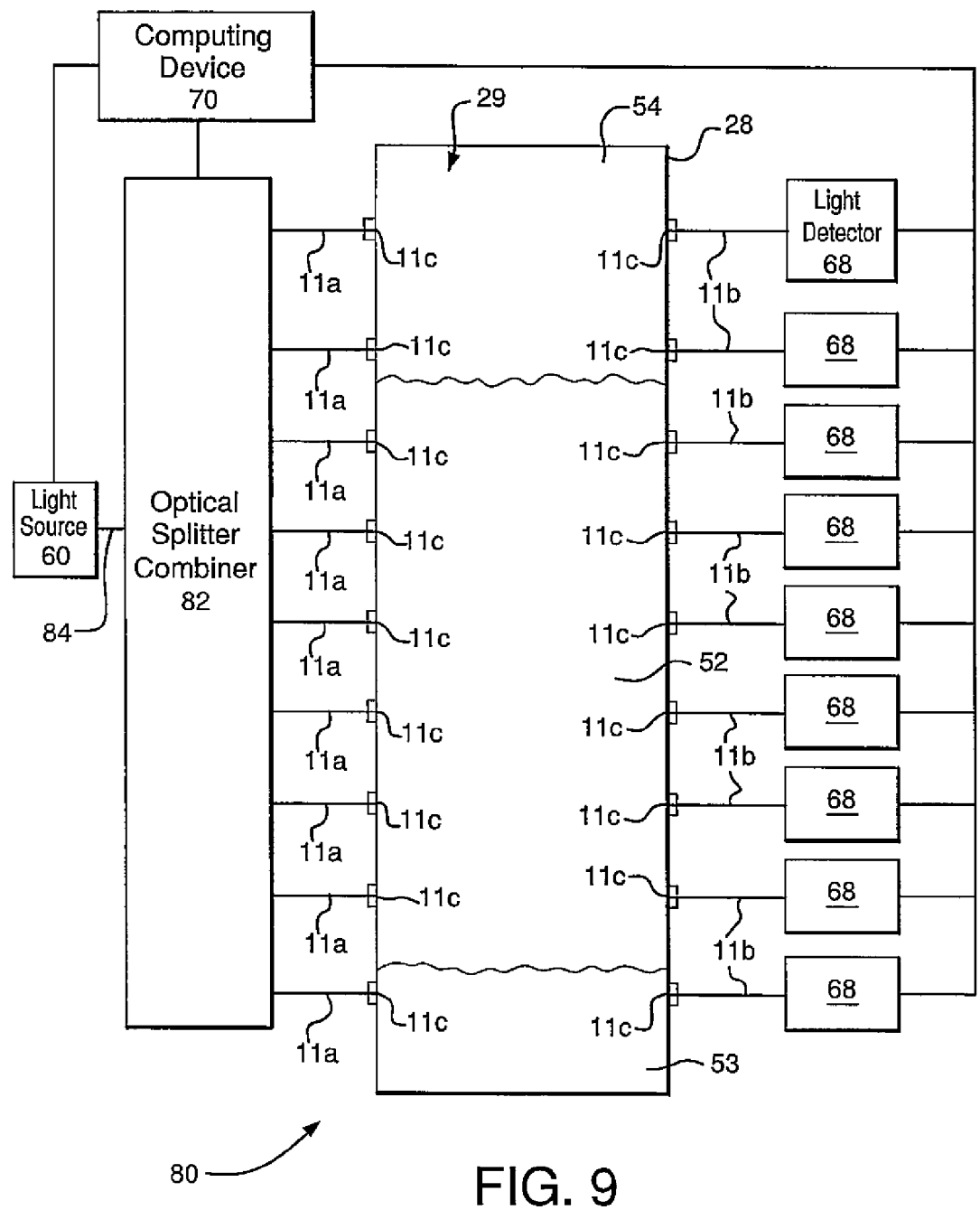
FIGS. 9-13 are block diagrams of various alternative embodiments of the system shown in FIGS. 1-7.

FIG. 9 depicts an alternative embodiment in the form of a system 80. Components common to the system 80 and the system 10 are denoted by identical reference characters.

The system 80 comprises a single light source 60, a bidirectional optical coupler 82, and multiple light detectors 68. The light source 60 is in optical communication with the optical coupler 82 by way of a fiber optic cable 84. The fiber optic cable 84 can be substantially identical to the fiber optic cables 11a, 11b.

The optical coupler 82 is in optical communication with each of the fiber optic cables 11a. The fiber optic cables 11a are routed into the housing 15 and the conduit 28 in the manner described above in relation to the system 10. The fiber optic cables 11b are routed from the conduit 28 and through the housing 15 in the manner described above in relation to the system 10. Each fiber optic cable 11b is in optical communication with an associated one of the light detectors 68.

The system 80 can operate in substantially the same manner as the system 10, with the following exception. The optical energy required to operate the system 80 is provided by the single light source 60, and is distributed to the various fiber optic cables 11a by the optical coupler 82.

Figure 10:
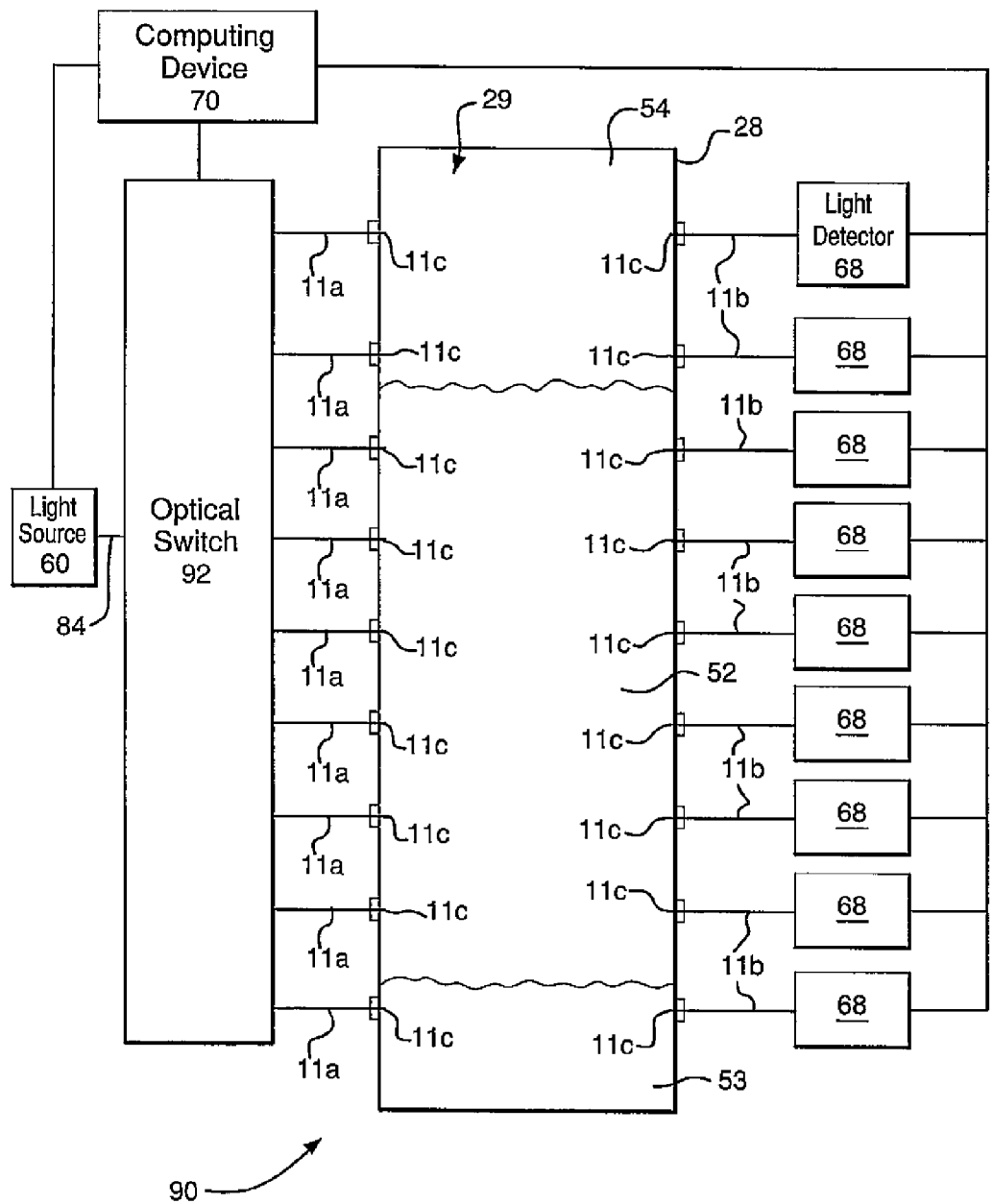

FIG. 10 depicts another alternative embodiment in the form of a system 90. Components common to the system 90 and the above-described systems are denoted by identical reference characters.

The system 90 comprises the single light source 60, an optical switch 92 communicatively coupled to the computing device 70, and multiple light detectors 68. The light source 60 is in optical communication with the switch 92 by way of a fiber optic cable 84. The optical switch 92 is in optical communication with each of the fiber optic cables 11a. The fiber optic cables 11a are routed into the housing 15 and the conduit 28 in the manner described above in relation to the system 10. The fiber optic cables 11b are routed from the conduit 28 and through the housing 15 in the manner described above in relation to the system 10. Each fiber optic cable 11b is in optical communication with an associated one of the light detectors 68.

The system 90 can operate in substantially the same manner as the system 10, with the following exception. The optical energy required to operate the system 90 is provided by the single light source 60, and is distributed to the various fiber optic cables 11a by the optical switch 92.

The computing device 70 can cycle the optical switch 92 so that the optical energy provided by the light source 60 is routed to each fiber optic cable 11a on a sequential basis.

The computing device 70 can be programmed to sample the output of the light detectors 68 sequentially. The computing device 70 can sample the output of a particular light detector 68 as the optical switch 92 is directing optical energy from the light source 60 to the fiber optic cable 11a associated with that particular light detector 68.

Figure 11:
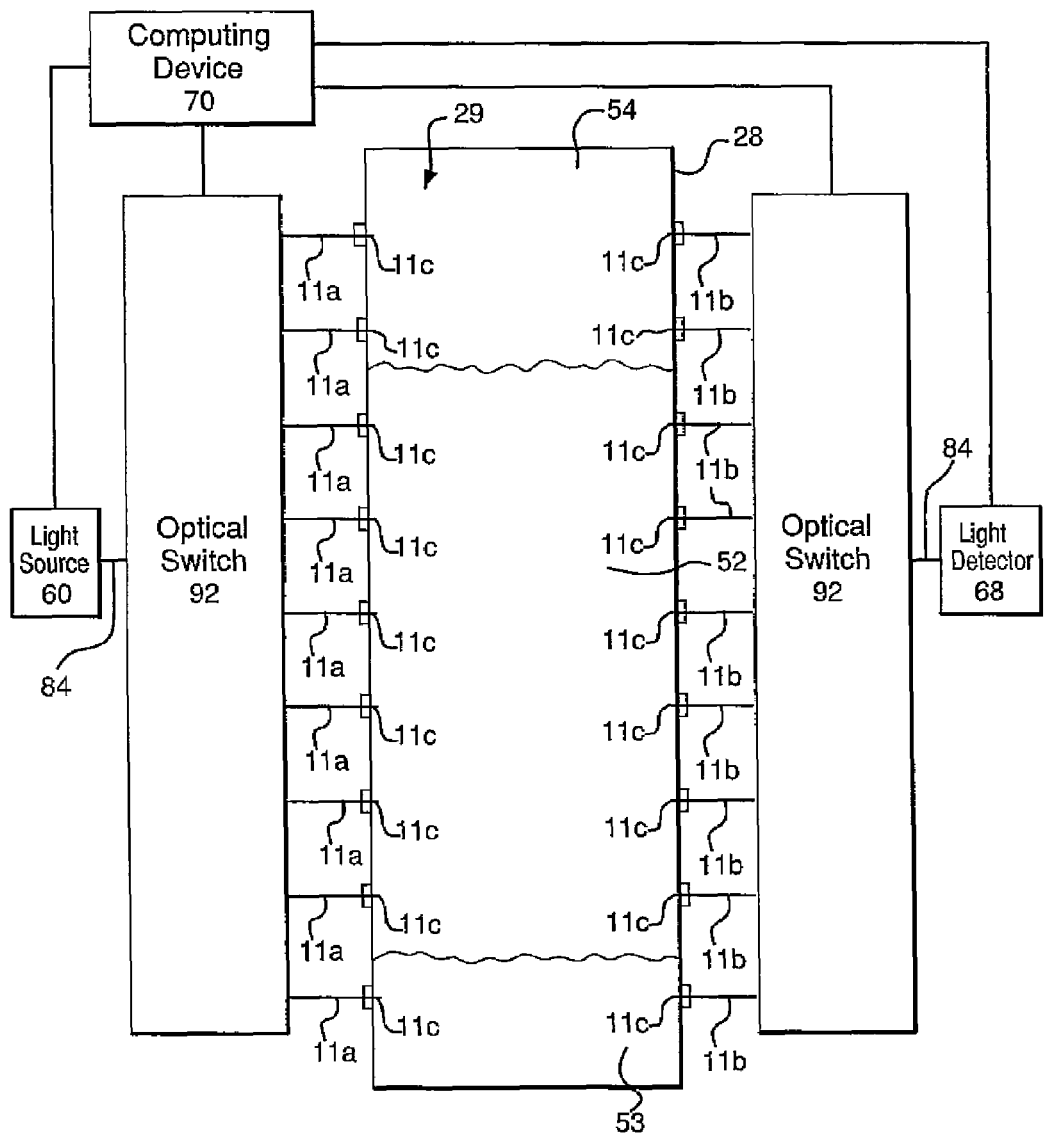

FIG. 11 depicts another alternative embodiment in the form of a system 100. Components common to the system 100 and the above-described systems are denoted by identical reference characters.

The system 100 comprises the single light source 60, a first and a second optical switch 92 communicatively coupled to the computing device 70, and a single light detector 68. The light source 60, the first optical switch 92, and the fiber optic cables 11a are configured in a manner substantially identical to the light source 60, optical switch 92, and fiber optic cables 11a of the system 90.

The fiber optic cables 11b are in optical communication with the second optical switch 92. The fiber optic cables 11b are routed from the conduit 28 and the housing 15 in the manner discussed above relation to the system 10. Each of the fiber optic cables 11b is in optical communication with the second optical switch 92. The second optical switch 92 is in optical communication with the light detector 68 by way of another of the fiber optic cables 84.

The first optical switch 92 can be cycled by the computing device 70 in the manner discussed above in relation to the system 90, so that the fiber optic cables 11a are in optical communication with the light source 60 on a sequential basis.

The computing device 70 can be programmed to cycle the first and second optical switches 92 in a corresponding manner. More particularly, the computing device 70 can coordinate the operation of the first and second optical switches 92 so that each fiber optic cable 11b is in optical communication with the light detector 68 when the associated fiber optic cable 11a is in optical communication with the light source 60.

Figure 12:
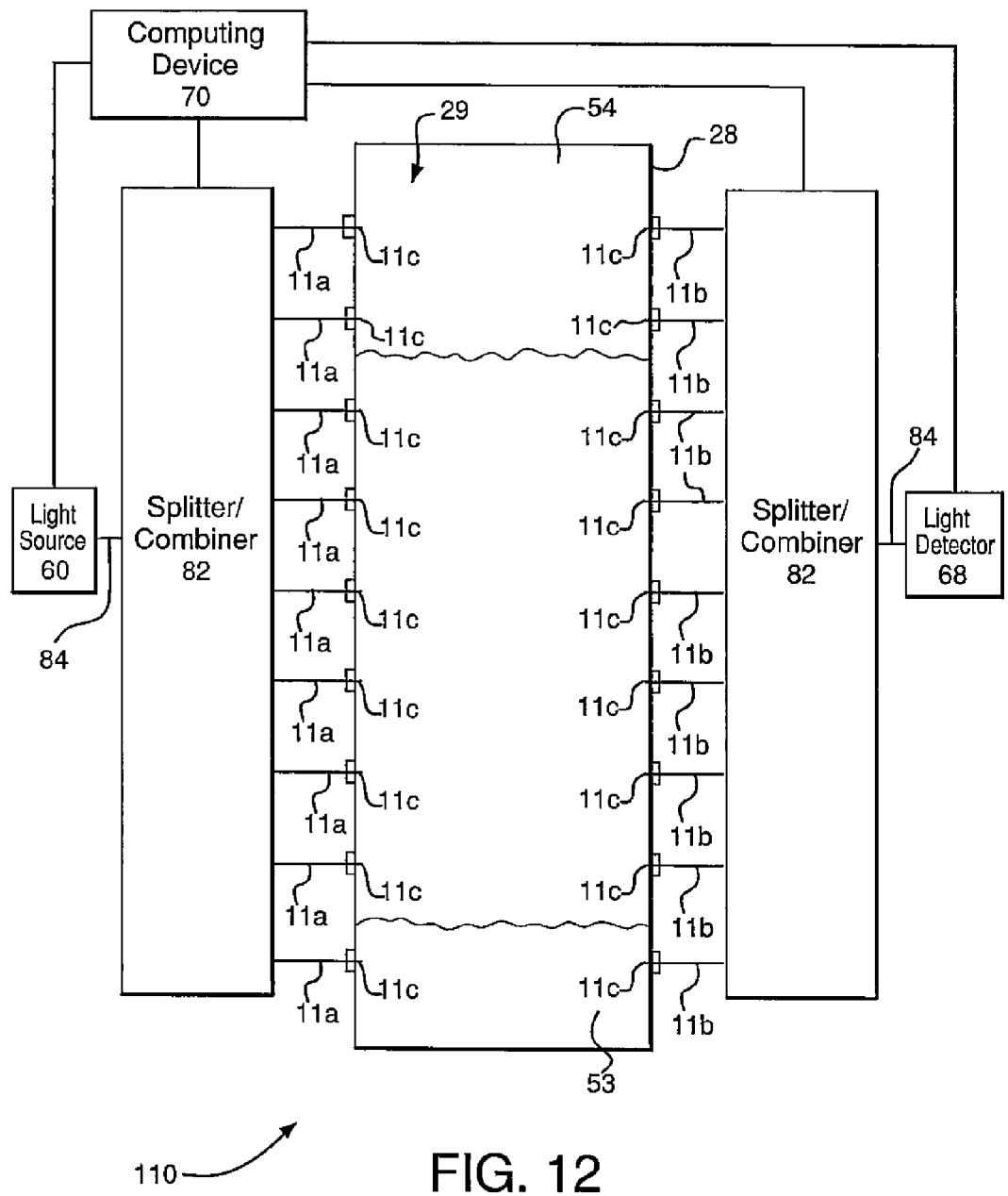

FIG. 12 depicts another alternative embodiment in the form of a system 110. Components common to the system 110 and the above-described systems are denoted by identical reference characters.

The system 110 comprises the single light source 60, a first and a second optical coupler 82, and a single light detector 68. The light source 60, the first optical coupler 82, and the fiber optic cables 11a are configured in a manner substantially identical to the light source 60, optical coupler 82, and fiber optic cables 11a of the system 80.

The fiber optic cables 11b are routed from the conduit 28 and the housing 15 in the manner discussed above relation to the system 10. The fiber optic cables 11b are in optical communication with the second optical coupler 82. The second optical coupler 82 is in optical communication with the light detector 68 by way of another of the fiber optic cables 84.

The second optical coupler 82 combines the optical energy transmitted through the fiber optic cables 11b. The combined optical energy is transmitted to the light detector 68, which generates a corresponding output.

The type of fluid present in each of the gaps 42 is related to the levels of the fluid 52 and water 53 in the tank 50, as discussed above in relation to the system 10. The type of fluid present in each gap 42 affects the amount of optical energy that is transmitted through the corresponding fiber optic cable 11b. The aggregate amount of optical energy transmitted through the fiber optic cables 11b and registered by the light detector 68 is therefore related to the fluid level in the tank 50.

A calibration can be performed to correlate the output the light detector 68 with the level of a specific type of fluid in the tank 50. The calibration results can be input to the computing device 70, so that the computing device 70 can recognize a particular output, or range of outputs for the light detector 68 as an indication of the fluid level in the tank 50. The calibration can be conducted over a range of temperatures, to account for temperature-related changes in the indexes of refraction of the fluid.

Figure 13:
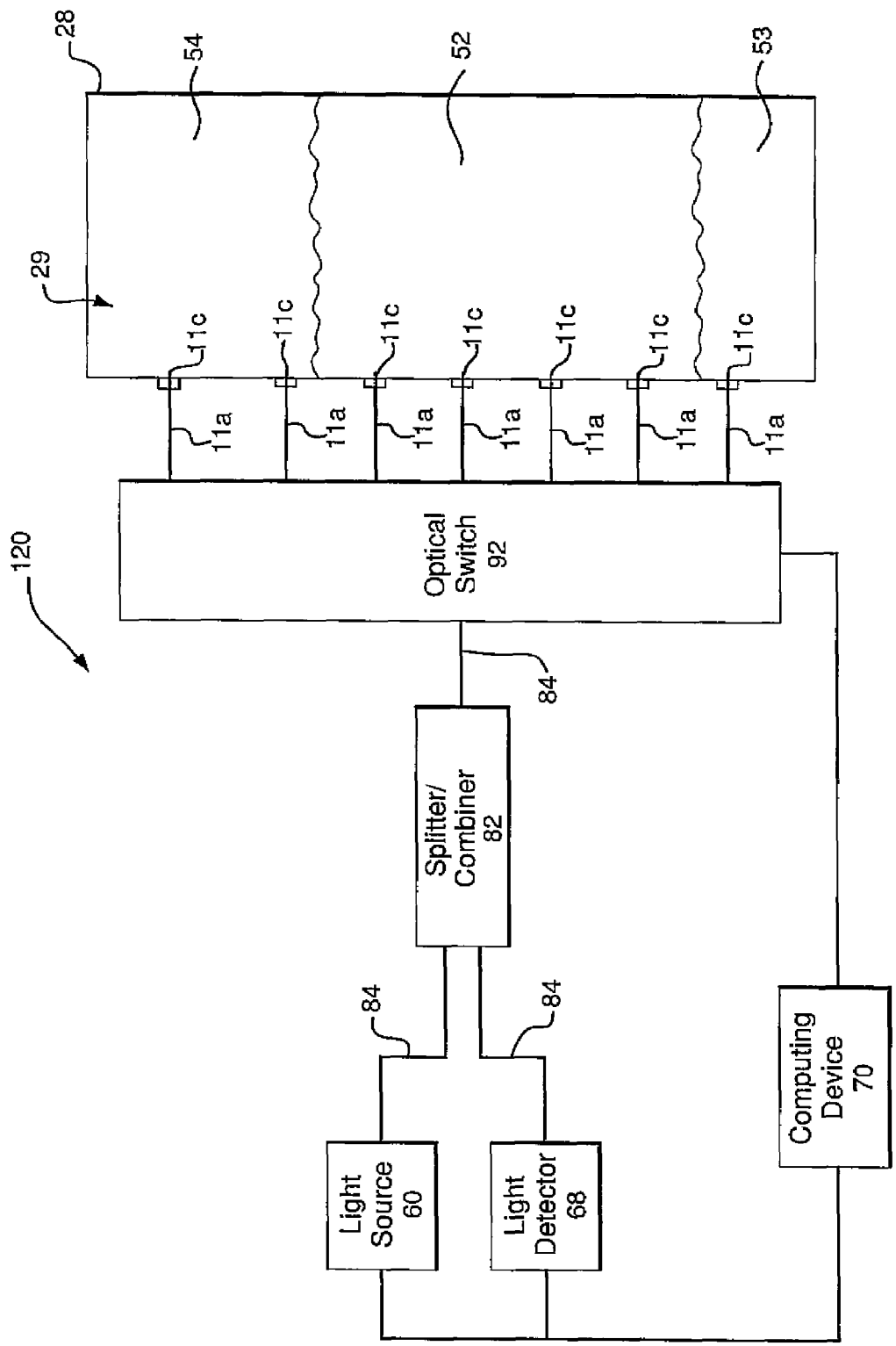

FIG. 13 depicts another alternative embodiment in the form of a system 120. Components common to the system 120 and the above-described systems are denoted by identical reference characters.

The system 120 comprises a single light source 60 and a single light detector 68. The 120 also comprises a bidirectional optical coupler 82, and an optical switch 92 communicatively coupled to the computing device 70. The light source 60 and the light detector 68 are in optical communication with the optical coupler 82 by way of respective fiber optic cables 84. The optical coupler 82 is in optical communication with the optical switch 92 by way of another fiber optic cable 84.

The system 120 further comprises a plurality of fiber optic cables 11a in optical communication with the optical switch 92. The fiber optic cables 11a are routed into the housing 15 and the conduit 28 in the manner discussed above in relation to the system 10.

A Fresnel reflection is generated when light is incident upon the interface of two materials having different indexes of refraction, as discussed in U.S. application Ser. No. 6b 11/649,109 titled "Methods and Systems for Determining the Density and/or Temperature of Fluids," filed on Jan. 3, 2007, the contents of which is incorporated by reference herein in its entirety. A Fresnel reflection therefore is generated at the interface of the optical fibers 17 of the fiber optic cables 11a, and the fluid or fluids in the tank 50. The reflected optical energy is transmitted to the optical coupler 82 by way of the fiber optic cables 11a. The optical coupler 82 directs a portion of the reflected optical energy to the light detector 68.

The computing device 70 can cycle the optical switch 92 so that the optical energy provided by the light detector 68 is routed to each fiber optic cable 11a on a sequential basis. The computing device 70 can also be programmed to recognize the output of the light detector 68 at a given instant as being associated with a particular fiber optic cable 11a having an end portion 11c that occupies a particular location in the conduit 28.

Each fiber optic cable 11a includes an optical fiber 17 having an end face 17a, as discussed above. The end portions 11c of the fiber optic cables 11a are stacked in a vertical arrangement within the passage 29 defined by the conduit 28, so that the end faces 17a are exposed to the fluid within the conduit 28.

The amount of optical energy reflected from the interface of each end face 17a and the fluid immersing the end face 17a due to the associated Fresnel reflection is related to the fluid type. Calibrations can be performed to correlate the output the light detector 68 with the presence of a particular type of fluid at the end faces 17a of the optical fibers 17. The calibration results can be input to the computing device 70, so that the computing device 70 can recognize a particular output, or range of outputs for the light detector 68 as an indication that fluid 52, water 53, air 54, or another type of fluid is present at the end face 17a of the optical fiber 17 of a particular fiber optic cable 11a. The calibration for each fluid can be conducted over a range of temperatures, to account for temperature-related changes in the indexes of refraction of the fluids.

The computing device 70 can programmed with the relative locations of the end faces 17a of the optical fibers 17 associated with each light detector 68. The location of each end face 17a can be referenced to a particular location along the height of the tank 50.

The computing device 70 can be programmed to identify the respective levels of the fluid 52 and water 53 based on the relative locations of the end faces 17a of the optical fibers 17, and the output level of the light detector 68. More particularly, the computing device 70 can be programmed to identify the uppermost end face 17a for which the light detector 68 generates an output indicative of the presence of fluid 52, based on the predetermined calibration data relating the output of the light detector 68 to a particular fluid type. The computing device 70 can also be programmed to identify the uppermost end face 17a associated with a light detector 68 whose output indicates the presence of water 53 at the end face 17a, based on the predetermined calibration data. The locations of the uppermost end faces 17a associated with the presence of fluid 52 and water 53 provide an indication of the approximate respective levels of the fluid 52 and water 53 in the tank 50.

Variants in the above-described configuration of the system 120 are possible. For example, one possible alternative embodiment (not shown) can include multiple pairs of light sources 60 and light detectors 68, and multiple bidirectional optical couplers 82. Each paired light source 60 and light detector 68 is in optical communication with an associated optical coupler 82. Each optical coupler 82 is in optical communication an associated one of the fiber optic cables 11a. This particular embodiment operates in substantially the same way as the system 120, with the following exceptions. Each fiber optical cable 11a continually transmits optical energy from a light source 60, and to a light detector 68 associated only with that particular fiber optic cable 11a.

Other variants (not shown) of the above-described configuration of the system 120 can include additional fiber optic cables 11a. The fiber optic cables 11a of this variant can be arranged in pairs, with the end faces 17a of each pair located at the same height within the passage 29. Each pair of fiber optic cables 11a can be connected to an optical coupler. Each optical coupler can be connected to an optical switch such as the optical switch 92 shown in FIG. 13. This arrangement combines the optical energy associated with two Fresnel reflections, i.e., the Fresnel reflections associated with the two fiber optic cables 11a in each pair. Pairing the fiber optic cables 11a in this manner can reduce the potential for relatively low-intensity reflections to be masked, especially in applications in which relatively high and low-intensity reflections are being transmitted through the fiber optical cables 11a, depending on the type of fluid in which the end portions 11c of the fiber optic cables 11a are immersed at a given time.

Figure 14:
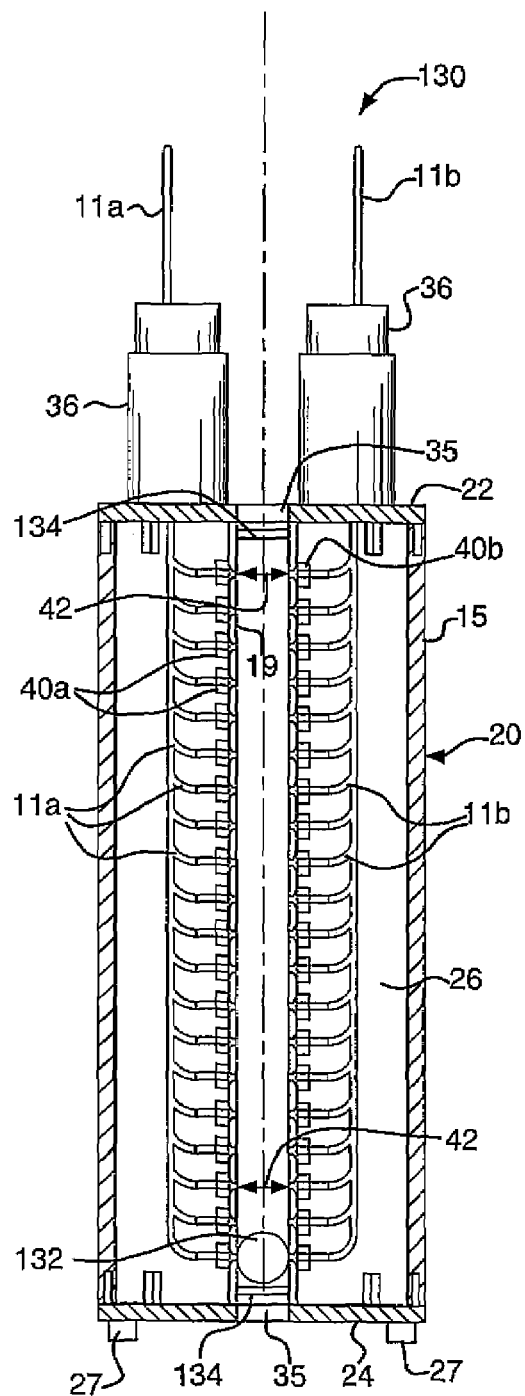
FIGS. 14 and 15 are cross-sectional views of a housing of another alternative embodiment of the system shown in FIGS. 1-7, taken from the same perspective as FIGS. 3 and 2, respectively.
Figure 15:
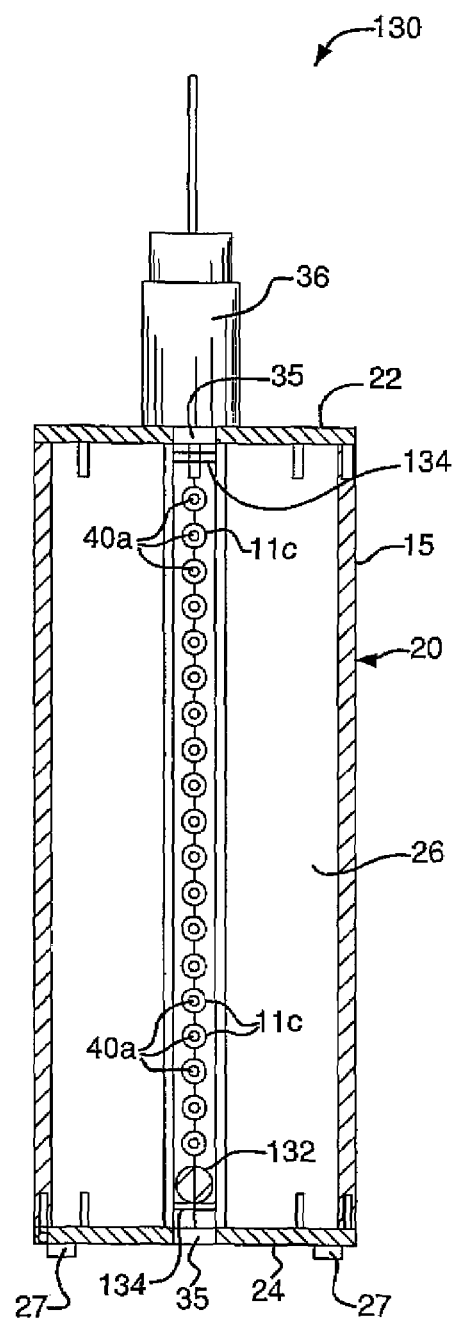

FIGS. 14 and 15 depict another alternative embodiment in the form of a system 130. The system 130 is substantially identical to the system 10, with the following exception. The system 130 includes a float 132 positioned in the passage 29 of the conduit 28. The float 132 is sized so that the float 132 can rise and fall with the level of fluid in the passage 29. The system 130 does not include the alignment guides 44 of the system 10. The top and bottom portions 22, 24 of the housing 15 or the conduit 28 can be equipped with pins 134 of other suitable means for preventing the float 132 from exiting the passage 29. The ball 132 is depicted in its lowermost position within the passage 29, thus indicating that the tank 50 is empty.

The float 132, when positioned between the end portions 11c of a corresponding pair of fiber optic cables 11a, 11b, blocks the transmission of optical energy across the associated gap 42. The output of a light detector 68 associated with a gap 44 that has been blocked by the float 132 will therefore be substantially lower than the outputs of the other light detectors 68. The computing device 70 can be programmed with the relative location of each fiber optic cable 11b in the stack of fiber optic cables 11b. The computing device 70 can be programmed to compare the outputs of the light detectors 68, and to recognize the location of the uppermost of the fiber optic cables 11b associated with a detector 68 having a relatively low output as the level of the fluid in the tank 50.

Alternative embodiments of the system 130 can incorporate a single light source 60, a single light detector 68, optical switches 92, and/or optical couplers 82 configured as in the systems 80, 90, 100, and/or 110.

The above-described systems can be used to determine the level of fluids in a tank or other type of container, and/or to identify the types of fluid or fluids in the tank without introducing electrical current into the fluids or the tank. The systems therefore do not introduce the potential for an explosion caused by the presence of a spark in or near the fluids, in contradistinction to electrical sensors used to measure dielectric constant. The systems can thus be used to determine the level and/or types of volatile, flammable fluids within a tank or other type of container, without introducing the potential to ignite flammable vapors of the fluid that may be present within the enclosed volume.

Moreover, the optical signals within the above-described systems are not subject to degradation due to electromagnetic interference, in contradistinction to electrical sensors.

The foregoing description is provided for the purpose of explanation and is not to be construed as limiting. While the embodiments have been described with reference to specific embodiments or methods, it is understood that the words which have been used herein are words of description and illustration, rather than words of limitation. Furthermore, although particular embodiments and methods have been described herein, the appended claims are not intended to be limited to the particulars disclosed herein. Those skilled in the relevant art, having the benefit of the teachings of this specification, may effect numerous modifications to the embodiments and methods as described herein, and changes may be made without departing from the scope of the appended claims.

For example, alternative embodiments of the systems described above can be constructed without the housing 15 and/or the conduit 28. For example, the end portions 11c of the fiber optic cables 11a and/or 11b can be mounted on the sides of the tank 52 in alternative embodiments, using the sleeves 40a, 40b or other suitable means.

A prototype system was constructed by Applicants to evaluate the attenuation of optical energy directed between opposing end faces of two optical fibers spaced apart by a gap, in the presence of different types of fluids. As discussed below, measurable differences between the optical energy traversing the gap in the presence of air and isopropyl alcohol were noted. Measurable differences between the optical energy traversing the gap in the presence of air and an alcohol/water mixture were likewise noted.

The prototype system included a light-emitting diode (LED) light source. The LED light source was connected to a first end of a first fiber optic cable using an SMA connector.

The first fiber optic cable was a three-foot long OZ QMMJ-55-IRVIS-940/1000-3-3 fiber optic cable. The light source produced an optical power level of 42.5 µW at a wavelength of 500 nm, measured at the end of the first fiber optic cable.

The optical power meter was connected to a first end of a second fiber optic cable using another SMA connector. The second fiber optic cable was an OZ QMMJ-55-IRVIS-940/1000-3-3-BL fiber optic cable.

An SMA connector was mounted on the second end of each of the first and second fiber optic cables, and a specially-designed fitting was installed on each SMA connector. The fittings were configured to mate in a manner that permitted the spacing, or gap between the end faces of the optical fibers of the first and second fiber optic cables to be adjusted.

During testing, optical energy was directed from the LED light source, and through the first fiber optic cable. The optical energy propagated across the gap between the end faces of the optical fibers of the first and second fiber optic cables, and was transmitted to the optical power meter by way of the second fiber optic cable. The gap between the end faces of the optical fibers was set at about 0.117 inches during testing.

A reading from the optical power meter was initially obtained while air was present in the gap between the end faces of the optical fibers, i.e., while the second ends of the first and second fiber optic cables were exposed to the ambient environment. The second ends, and the associated fittings, were subsequently lowered into a container of liquid so that the gap was filled by the liquid. A reading from the optical power meter was then obtained. The second ends were subsequently removed from the liquid, and the above procedure was repeated at least once.

Testing was conducted using the following liquids: (i) water; (ii) 99% isopropyl alcohol; (iii) a mixture of 50% isopropyl alcohol and 50% water, by volume; and (iv) Jet A aviation fuel.

Consistent and repeatable results were obtained when the second ends of the fiber optic cables were immersed in the 99% alcohol, and the alcohol/water mixture. The optical power meter registered an average of about 20.55 µW with a standard deviation of about 0.25 µW when the second ends were immersed in the 99% alcohol. The optical power meter registered an average of about 11.14 µW with a standard deviation of about 0.29 µW, when air was present in the gap prior to immersion in the alcohol.

The optical power meter registered an average of about 19.11 µW with a standard deviation of about 0.26 µW, when the second ends were immersed in the water/alcohol mixture. The optical power meter registered an average of about 9.79 µW, with a standard deviation of about 0.64 µW, when air was present in the gap prior to immersion in the water/alcohol mixture.

Consistent and repeatable results were not obtained when the prototype system was tested using water and Jet A fuel. It is believed that the results of this testing were affected by the propensity for a film of the water or fuel to remain on the end faces of the optical fibers after the end faces were removed from the water or fuel. It is believed that improvements in the performance of the system can potentially be achieved by measures that reduce the propensity of the fluid to adhere to the end faces. These measures can include, for example, coating the end faces, placing a convex or other type of lens over each end face; shaping the end faces in a convex or other manner; increasing the cross-sectional area of the optical fibers; and adjusting the spacing between the end faces to force fluid away from the end faces through capillary action. In addition, performance improvements may potentially be obtained by choosing an optimal wavelength, or range of wavelengths for the light emitted by the source of optical energy.

What is claimed is:

1. A system, comprising:
   a first plurality of optical waveguides each having an end face capable of being immersed in one or more types of fluids in a container;
   a second plurality of optical waveguides each having an end face that opposes an associated end face of one of first plurality of optical waveguides and is spaced apart from the associated end face of the one of first plurality of optical waveguides by a gap;
   one or more sources of optical energy in optical communication with the first plurality of optical waveguides;
   one or more detectors of optical energy in optical communication with the second plurality of optical waveguides; and
   a computing device communicatively coupled to the one or more detectors of optical energy, wherein the computing device is capable of determining a level of the fluid in the container based on an intensity of the optical energy incident upon the one or more detectors of optical energy and relative locations of the end faces of the first and/or second plurality of optical waveguides, and wherein the system comprises only one of the sources of optical energy and only one of the detectors of optical energy and the system further comprises: (i) a first optical switch in optical communication with the source of optical energy and a first set of the optical waveguides, and communicatively coupled to the computing device: and (ii) a second optical switch in optical communication with the detector of optical energy and a second set of the optical waveguides, and communicatively coupled to the computing device, wherein the computing device coordinates the operation of the first and second optical switches so that the first optical switch places each of the optical waveguides in the first set of the optical waveguides in optical communication with the source of optical energy as the second optical switch places an associated one of the optical waveguides of the second set of the optical waveguides in optical communication with the detector of optical energy.

2. The system of claim 1, wherein the end faces of the first plurality of optical waveguides are arranged in a stacked relationship, and the end faces of the second plurality of optical waveguides are arranged in a stacked relationship.

3. The system of claim 2, wherein the end faces of the first plurality of optical waveguides are aligned in the vertical direction, and the end faces of the second plurality of optical waveguides are aligned in the vertical direction.

4. The system of claim 1, further comprising a housing capable of being immersed in the one or more fluids in the container, wherein the end faces of the first and second pluralities of optical fibers are positioned within the housing.

5. The system of claim 4, wherein the housing comprises a conduit, the end faces of the first and second pluralities of optical fibers are positioned within a passage defined by the conduit, and ends of the passage are open so that the one or more types of fluids in the container can enter and exit the passage and the levels of the one or more types of fluids can rise and fall within the passage with the levels of the one or more types of fluids within the container.

6. The system of claim 5, further comprising a plurality of sleeves mounted on the conduit, wherein each of the optical waveguides extends into the passage through an associated one of the sleeves.

7. The system of claim 6, wherein: the housing further comprises a body, and a top and a bottom portion secured to the body; the body and the top and bottom portions define a volume within the housing, and the conduit is positioned within the volume.

8. The system of claim 7, wherein the top and bottom portions each have a through hole formed therein that aligns with an associated one of the ends of the passage.

9. The system of claim 8, wherein the first plurality of the optical waveguides extend into the volume by way of a first through hole formed in the top portion of the housing, and a second plurality of the optical waveguides extend into the volume by way of a second through hole formed in the top portion of the housing.

10. The system of claim 9, further comprising a first and a second sleeve, wherein the first and second sleeves are received by the respective first and second through holes formed in the top portion of the housing, the first plurality of optical waveguides extend into the volume by way of the first sleeve, and the second plurality of optical waveguides extend into the volume by way of the second sleeve.

11. The system of claim 1, wherein the system further comprises an optical coupler in optical communication the source of optical energy and the first set of optical waveguides.

12. The system of claim 1, wherein the system further comprises an optical coupler in optical communication with the detector of optical energy and the second set of optical waveguides.

13. The system of claim 1, wherein the system comprises an optical coupler in optical communication with the source of optical energy and the detector of optical energy.

14. The system of claim 1, wherein the optical waveguides are optical fibers.

15. The system of claim 1, further comprising a float, where the float can be positioned in the gaps between the associated end faces of the first and second pluralities of optical waveguides so that the float blocks transmission of the optical energy between the associated end faces of the first and second pluralities of optical fibers.

16. The system of claim 15, further comprising a housing capable of being immersed in the one or more fluids in the container, wherein the housing comprises a body and a conduit positioned within the body, the conduit defines a passage, the end faces of the optical waveguides are positioned in the passage, ends of the passage are open so that the one or more types of fluids in the container can enter and exit the passage and the levels of the one or more types of fluids can rise and fall within the passage with the levels of the one or more types of fluids within the container, and the float is positioned within the passage so that the float can rise and fall with the levels of the one or more fluids in the passage.

* * * * *